United States Patent [19]

Imai

[11] 4,317,923
[45] Mar. 2, 1982

[54] PURIFICATION OF DICARBOXYLIC AROMATIC ACIDS

[75] Inventor: Tamotsu Imai, Mount Prospect, Ill.

[73] Assignee: UOP Inc., Des Plaines, Ill.

[21] Appl. No.: 189,386

[22] Filed: Sep. 19, 1980

Related U.S. Application Data

[63] Continuation-in-part of Ser. No. 69,019, Aug. 23, 1979, abandoned.

[51] Int. Cl.³ .............................................. C07C 51/42
[52] U.S. Cl. .................................................. 562/487
[58] Field of Search .......................................... 562/487

[56] References Cited

U.S. PATENT DOCUMENTS

| | | | |
|---|---|---|---|
| 3,151,154 | 9/1964 | Sargent et al. | 260/525 |
| 3,456,001 | 7/1969 | Olsen | 260/525 |
| 3,522,298 | 7/1970 | Bryant, Jr. et al. | 260/525 |
| 3,546,285 | 12/1970 | Witt | 260/525 |
| 3,607,921 | 9/1971 | Stancell et al. | 260/525 |

OTHER PUBLICATIONS

Cotton "Advanced Inorg. Chem.", 2nd Ed., (1966) p. 965.

*Primary Examiner*—A. Siegel
*Attorney, Agent, or Firm*—James R. Hoatson, Jr.; Raymond H. Nelson; William H. Page II

[57] ABSTRACT

Dicarboxylic aromatic acids containing impurities such as aldehydes may be purified by treating the acids at an elevated temperature in the presence of a catalyst containing metallic rhenium whereby the impurities may be removed and the purified acids recovered.

9 Claims, No Drawings

PURIFICATION OF DICARBOXYLIC AROMATIC ACIDS

CROSS REFERENCE TO RELATED APPLICATIONS

This application is a continuation-in-part of my co-pending application, Ser. No. 69,019 filed Aug. 23, 1979, now abandoned, more teachings of which are included herein with reference thereto.

BACKGROUND OF THE INVENTION

Dicarboxylic aromatic acids such as phthalic acid, isophthalic acid and terephthalic acid may be prepared by an oxidation process in which mixed alkyl aromatics or particular xylenes are subjected to an oxidation reaction with heavy metal salts and bromine acting as catalysts. For example, paraxylene may be oxidized to terephthalic acid in the liquid phase with a catalyst consisting of cobalt acetate and hydrogen bromide dissolved in acetic acid. An oxygen containing gas such as air is injected into the reactor which is maintained at an elevated temperature of around 200° C. and superatmospheric pressures of about 10 atomspheres. The amount of air which is injected into the reactor is sufficient to maintain an excess of oxygen in the off-gas over the stoichiometric requirement. The liquid which is drawn from the reactor will contain about 25 to about 35 percent solids. These solids contain the desired terephthalic acid as well as a contaminant or impurity in the form of paracarboxybenzaldehyde, an intermediate in the formation of terephthalic acid. As the reaction proceeds and the terephthalic acid crystallizes out of the reaction medium, it entrains with it the solid paracarboxybenzaldehyde in the form of mixed crystals, thereby retaining the further oxidation of impurity difficult to achieve.

In the past, the working up and purification of terephthalic acid has presented considerable problems inasmuch as the aforesaid paracarboxybenzaldehyde is a difficult compound to remove by the usual purification methods. In view of the greater solubility of paracarboxybenzaldehyde in acetic acid relative to terephthalic acid, the amount of impurity in the terephthalic acid will be greatly reduced but will still be in excess of the maximum amount allowable in the acid. Therefore, it is necessary to utilize a relatively complex purification system including various steps such as oxidation, neutralization, recycling, washing, distillation, etc.

Several U.S. patents have disclosed methods for purifying acids, and particularly aromatic dicarboxylic acids. For example, U.S. Pat. No. 3,546,285 discloses a method for purifying aromatic dicarboxylic acids such as terephthalic acid by catalytically hydrogenating the acid which is dissolved in a solvent at an elevated temperature. The catalytic hydrogenation compound which is employed in this process comprises a noble or other metal of Group VIII of the Periodic Table such as platinum, palladium, nickel, etc. Likewise, U.S. Pat. No. 3,151,154 is drawn to a method for decolorizing phthalic acids or salts thereof which have been prepared by the nitric acid oxidation of diloweralkyl benzenes and loweralkyl benzoic acids by reducing the nitro compounds in a liquid polar solvent in the presence of a solid Group VIII metal hydrogenation catalyst and thereafter acidifying the resulting reduced product.

U.S. Pat. No. 3,607,921 utilizes a process for purifying terephthalic acid by contact, in the presence of carbon monoxide, with solid particles of an adsorptive agent which possesses substantial carbon monoxide sorption capacity, while U.S. Pat. No. 3,456,001 purifies these acids by utilizing a support Group VIII noble metal catalyst such as platinum, palladium, ruthenium, rhodium, iridium, and osmium.

Yet another patent which teaches a purification process is U.S. Pat. No. 3,522,298. This patent teaches the purification of terephthalic acid by contacting a vaporous mixture and a gaseous medium with a solid material comprising a Group VIII metal, said gaseous medium comprising either hydrogen or oxygen.

As will hereafter be shown in greater detail, it has now been discovered that it is possible to remove contaminants or impurities from dicarboxylic aromatic acids in a relatively inexpensive and simple manner, said method involving the catalytic decarbonylation of contaminants utilizing a catalyst comprising a metallic rhenium containing compound while effecting the reaction in a liquid phase without requiring the presence of either hydrogen or oxygen.

DETAILED DESCRIPTION OF THE INVENTION

This invention relates to a process for the purification of dicarboxylic aromatic acids. More specifically, the invention is concerned with the process for removing contaminants such as intermediate products which have not been fully oxidized and which are present in dicarboxylic aromatic acids, the latter having been prepared by the direct oxidation of alkyl aromatic compounds.

Dicarboxylic aromatic acids such as phthalic acid, isophthalic acid and terephthalic acid will find a wide variety of uses in the chemical field. For example, phthalic acid is used in dyes, especially in the synthesis of indigo, in the manufacture of phthaleins, various fluorescein and eosin dyes, as well as in the manufacture of rhodamines and pyronine dyes. In addition, it is also used in the manufacture of various medicines and synthetic perfumes. Isophthalic acid is used in the manufacture of polyester and polyurethane resins as well as a component of plasticizers. Terephthalic acid is used as a reagent for alkali in wool as well as in the production of synthetic resins, fibers and films by combination with glycols, said synthetic materials being sold under the tradenames of Dacron, Mylar, Terylene, etc. However, in order to utilize these acids, it is necessary that the same be in a relatively pure state and not contain an inordinant amount of contaminants or impurities.

The present process involves a method for purifying dicarboxylic aromatic acids by decarbonylation of aldehyde impurities as exemplified by paracarboxybenzaldehyde, by utilizing a metallic rhenium containing catalyst. The present process differs from the prior art which involved the removal of impurities from such acids by utilizing a hydrogenation reaction. In addition to using a hydrogenation process which involved the presence of Group VIII metal catalysts to effect the desired reaction, it is also known that rhenium compounds and particularly rhenium sulfide may be used as catalysts for hydrogenation reactions. However, rhenium sulfide cannot be used as a catalyst in the present invention which involves the use of metallic rhenium, inasmuch as sulfur poisons metallic rhenium and therefore would render the metallic rhenium containing catalyst inoperative for effecting the desired decarbonylation reaction.

It is therefore an object of this invention to provide a method for the purification of dicarboxylic aromatic acids.

A further object of this invention is to provide a method for the purification of dicarboxylic aromatic acids by treating said acids with certain rhenium containing compounds.

In one aspect an embodiment of this invention resides in a process for the purification of a dicarboxylic aromatic acid containing impurities therewith which comprises treating said acid in the presence of a catalyst comprising a rhenium containing compound at treatment conditions, and recovering the purified dicarboxylic aromatic acid.

A specific embodiment of this invention is found in the process for purification of terephthalic acid which comprises treating said acid in an aqueous medium in the presence of a catalyst comprising metallic rhenium deposited on carbon at a temperature in the range of from about 150° to about 350° C. and in the presence of a nitrogen atmosphere and recovering the purified terephthalic acid.

Other objects and embodiments will be found in the following further detailed description of the invention.

As hereinbefore set forth, the present invention is concerned with a process for the purification of dicarboxylic aromatic acids, and particularly the isomeric phthalic acids. The purification of these acids to remove contaminants or impurities such as partially oxidized compounds as exemplified by aldehydes is effected by treating the impurities containing acid in an aqueous medium in the presence of a catalyst which contains metallic rhenium. The purification of the acid is effected at elevated temperatures which may range from about 150° up to about 350° C. or more. In addition, the purification may also be effected by pressures which may range from about 1 to about 100 atmospheres. If superatmospheric pressures are employed, they may be afforded by the introduction of a gas into the reaction vessel, said gas being inert in nature such as argon, helium, etc.

The catalytic composition of matter which is utilized to effect the reaction will comprise a metallic rhenium containing compound, and if so desired, this metallic rhenium compound may be dispersed on a solid material. Some specific examples of solid supports which are utilized include refractory oxides such as alumina, silica, mixtures of refractory oxides such as alumina-silica, alumina-zirconia, silica-zirconia, alumina-zirconia-magnesia, etc, silicon carbide, carbon, etc. In addition, if so desired, the catalyst may also be modified to include at least one element selected from Group VIII of the Periodic Table, said Group VIII metal being utilized to increase the catalytic activity and stability of the catalyst. Examples of Group VIII metals which may be employed will include in particular the noble metals such as platinum, palladium, ruthenium, osmium and iridium. It is also contemplated within the scope of this invention that the non-noble metals such as iron, nickel, and cobalt may also be employed. However, it is to be understood that the catalytic activities to effect the decarbonylation of the impure components which are present in the dicarboxylic aromatic acid is afforded by the metallic rhenium, and that the Group VIII metals are present merely as modifiers.

The process of this invention may be effected in any suitable manner and may comprise either a batch or continuous type of operation. For example, when a batch type of operation is to be employed, a quantity of the particular dicarboxylic aromatic acid which is to be purified is placed in an appropriate apparatus along with the metallic rhenium containing catalyst and water. Inasmuch as the reaction is to be effected at superatmospheric pressures, the preferred type of vessel which is employed will comprise one that is pressure resistant such as autoclaves of the rotating, stirring, or mixing type, etc. The vessel is then sealed and a gas which may be inert or reducing in nature is charged to the vessel until the desired operating pressure is attained. Thereafter, the vessel and contents thereof are heated to the desired operating temperature and maintained thereat for a predetermined period of time which may range from about 0.5 up to about 10 hours or more in duration. Upon completion of the desired residence time, heating is discontinued and after the vessel has returned to room temperature the excess pressure is discharged. The vessel is then opened and the reaction mixture is recovered therefrom, the purified acid being separated from the catalyst and water by conventional means such as filtration, decantation, fractional distillation, etc.

It is also contemplated within the scope of this invention that purification of the dicarboxylic aromatic acid may be effected in a continuous manner of operation. When this type of operation is employed, the impure acid is continously charged to a reactor which is provided with the particular catalytic composition of matter utilized in the treatment, said reactor being maintained at the proper operating conditions of temperature and pressure hereinbefore set forth. The water which supplies the aqueous medium in which the reaction is effected may also be continuously supplied to the reactor through a separate line or, if so desired, it may be admixed with the acid and the slurry charged thereto in a single stream. Upon completion of the desired residence time, the reactor effluent is continuously withdrawn from the reactor and subjected to conventional means of separation of the type hereinbefore set forth whereby the purified acid may be separated and recovered.

The following examples are given for purposes of illustrating the process of this invention. However, it is to be understood that these examples are illustrative of the process and that the invention is not necessarily limited thereto.

EXAMPLE I

A catalyst for the treatment of dicarboxylic aromatic acids to remove impurities therefrom was prepared by impregnating 500 cc of silica gel with a solution consisting of 350 ml of water, 10 cc of hydrochloric acid, 56.75 ml of palladium chloride containing 30 mg of palladium/ml and 119.17 ml of ammonium perrhenate containing 25 mg of rhenium/ml, said impregnation being accomplished in a rotary evaporator. After impregnation the catalyst was removed from the rotary evaporator and dried at a temperature of 120° C.

The purification of terephthalic acid was accomplished by treating 10 grams of terephthalic acid which contained 7800 ppm of paracarboxybenzaldehyde along with 2 grams of the catalyst prepared according to the above paragraph and 100 ml of water in a rotating autoclave. The autoclave was sealed and air in the autoclave was replaced with nitrogen at an initial operating pressure of 1 atmosphere. The autoclave was then heated for a period of 1 hour at a temperature of 250° C. At the end of this period heating was discontinued and after the autoclave was returned to room temperature the pressure was vented and the reaction mixture was recovered. It was determined by polarography that the terephthalic acid after treatment contained 200 ppm of paracarboxybenzaldehyde.

EXAMPLE II

In the example, ammonium perrhenate was dissolved in water in a rotary evaporator to form 20 ml of a solution containing 100 mg of rhenium/ml of solution. Following this, 100 cc of carbon was added to the solution and impregnated with the ammonium perrhenate solution at steam temperature. After impregnation, the sample was removed from the rotary evaporator and dried at 120° C. Following this the catalyst was reduced at a temperature of 400° C. for a period of 2 hours in a stream of hydrogen to form metallic rhenium.

Purification of the acid was accomplished by treating 100 grams of crude terephthalic acid containing 7800 ppm of paracarboxybenzaldehyde with 1 gram of the catalyst and 100 cc of water in an autoclave under 1 atmosphere of nitrogen for a period of 1 hour at 250° C. At the end of this period heating was discontinued and after opening the autoclave the reaction mixture was filtered and dried at 120° C. Analysis of the sample by polarography showed that the acid contained 2500 ppm of paracarboxybenzaldehyde.

EXAMPLE III

In this example, 1 gram of the metallic rhenium catalyst which was prepared according to Example II above was ground to 8/20 mesh and used to treat 10 grams of crude terephthalic acid containing 7800 ppm of paracarboxybenzaldehyde (PCB). The acid and catalyst along with 100 ml of water was treated at a temperature of 250° C. for a period of 1 hour. At the end of this period the sample was dissolved in the water phase by adding an aqueous solution of sodium carbonate. Following this, the solution was filtered and converted into terephthalic acid by the addition of an aqueous solution of hydrochloric acid. The solid terephthalic acid was washed with water and dried at a temperature of 120° C. for a period of 1 hour. Analysis of the sample showed a PCB level of 1400 ppm. In addition, chemical analysis of the treated sample disclosed that it did not contain any rhenium.

When the catalyst was ground to a particle size of less than 100 mesh and used to treat 10 grams of crude terephthalic acid similar in nature to that described in the above paragraph under similar conditions, analysis of the treated sample disclosed a PCB level of 130 ppm.

EXAMPLE IV

A catalyst for the treatment of dicarboxylic aromatic acids was prepared by dissolving 14.35 ml of palladium chloride containing 30.7 mg of palladium/ml, 22.10 ml of ammonium perrhenate containing 100 mg of rhenium/ml and 5 ml of concentrated hydrochloric acid in 100 ml of water in a rotary evaporator. Thereafter 100 cc of charcoal having an apparent bulk density of 0.442 was added to the solution and impregnation was accomplished at steam temperature. Following impregnation, the catalyst was then dried at 120° C. for a period of 16 hours. Following the drying, the catalyst was then reduced in a stream of hydrogen at a temperature of 400° C. for a period of 2 hours to form metallic rhenium.

Purification of crude terephthalic acid containing 7800 ppm of PCB was effected by treating 10 grams of the acid with 1 gram of the catalyst which contained 1% palladium and 5% of metallic rhenium on the carbon along with 100 ml of water for a period of 1 hour at a temperature of 250° C. At the end of the reaction time, the sample was dissolved in the water phase by adding an aqueous solution of sodium carbonate. After filtration, an aqueous solution of hydrochloric acid was added and the sample was converted to terephthalic acid. After washing the sample with water and drying at a temperature of 120° C. for a period of 1 hour, analysis disclosed that the purified terephthalic acid contained only about 100 ppm of PCB.

When 1 gram of the catalyst prepared according to the example was ground to less than 100 mesh and used to treat 10 grams of crude terephthalic acid containing 7800 ppm PCB in a manner similar to that set forth in the above paragraph, it was found that the PCB level of the treated acid was less than 10 ppm and in addition, the treated sample did not contain any rhenium.

EXAMPLE V

In this example, a catalyst similar in nature to that set forth in Example IV above was prepared by impregnating 100 cc of charcoal with a solution consisting of 100 ml of water, 5 ml of concentrated hydrochloric acid, 7.74 ml of ammonium perrhenate and 14.39 ml of palladium chloride. The catalyst after impregnation, drying and reduction contained 1% palladium and 1.75% of metallic rhenium composited on carbon.

When 1 gram of this catalyst was used to treat 10 grams of crude terephthalic acid containing 7800 ppm PCB in 100 ml of water in a manner similar to that set forth in the above examples, the resulting terephthalic acid, after treatment thereof, was found to contain 105 ppm PCB.

When the catalyst was ground to less than 100 mesh and used in a manner identical to that set forth above, the treated terephthalic acid was found to contain less than 10 ppm PCB as determined by polarography.

EXAMPLE VI

In this example, 14.21 ml of a platinum solution containing 31.1 mg of platinum/ml, 4.22 ml of ammonium perrhenate containing 100 mg of rhenium/ml, and 5 ml of concentrated hydrochloric acid were dissolved in 100 ml of water in a rotary evaporator. Thereafter 100 cc of charcoal was added to the solution and impregnated at steam temperature. The impregnated sample was dried at a temperature of 120° C. for a period of 16 hours and reduced in a stream of hydrogen at 400° C. for a period of 2 hours to form metallic rhenium. Crude terephthalic acid containing 7800 ppm PCB in an amount of 10 grams was treated with 1 gram of this catalyst along with 100 ml of water at a temperature of 250° C. for a period of 1 hour. The recovered sample was treated with sodium carbonate and hydrochloric acid in a manner similar to that set forth in the above examples and the recovered terephthalic acid was found to contain 92 ppm PCB by polarography.

When 1 gram of the catalyst prepared according to this example was ground to less than 100 mesh and used to treat crude terephthalic acid in a similar manner, the treated sample was found to contain 220 ppm PCB.

EXAMPLE VII

In this example, a catalyst which contained 1% palladium and 5% metallic rhenium was prepared in a manner similar to that set forth in Example VI above. The treatment of crude terephthalic acid containing 7800 ppm of PCB was accomplished by utilizing 1 gram of catalyst particles and 100 ml of water. A sample was treated in a manner similar to that set forth in the above examples and after recovery was found to contain 88 ppm of PCB.

When the catalyst was ground to less than 100 mesh and used to treat a similar sample of terephthalic acid, the treated acid after recovery was found to contain 48 ppm PCB.

I claim as my invention:

1. A process for the purification of an acid selected from the group consisting of phthalic, isophthalic, and terephthalic acids containing paracarboxybenzaldehyde as an impurity, which comprises contacting said acid in an aqueous medium with a catalyst comprising metallic rhenium at a temperature of from about 150° to about 350° C. to effect decarbonylation of said paracarboxybenzaldehyde and recovering the thus purified acid.

2. The process as set forth in claim 1 in which said purification is effected in an inert atmosphere.

3. The process as set forth in claim 2 in which said inert atmosphere is afforded by nitrogen.

4. The process as set forth in claim 1 in which said metallic rhenium is deposited on a solid support.

5. The process as set forth in claim 4 in which said metallic rhenium is deposited on carbon.

6. The process as set forth in claim 4 in which said catalyst comprises metallic rhenium deposited on alumina.

7. The process as set forth in claim 1 in which said acid is phthalic acid.

8. The process as set forth in claim 1 in which said acid is isophthalic acid.

9. The process as set forth in claim 1 in which said acid is terephthalic acid.

* * * * *